(12) United States Patent
Ignotz et al.

(10) Patent No.: US 9,877,647 B2
(45) Date of Patent: Jan. 30, 2018

(54) DEVICE FOR DETECTION OF DIABETES

(75) Inventors: Keith D. Ignotz, Charlottesville, VA (US); Dale A. Rorabaugh, Healdsburg, CA (US); Neil M. Davis, Temecula, CA (US); Vincent F. Brancaccio, Eugene, OR (US); Paul Williams, La Jolla, CA (US); Craig H. Misrach, San Diego, CA (US)

(73) Assignee: Sinocare Meditech, Inc., Changsha (CN)

( * ) Notice: Subject to any disclaimer, the term of this patent is extended or adjusted under 35 U.S.C. 154(b) by 0 days.

(21) Appl. No.: 13/291,074

(22) Filed: Nov. 7, 2011

(65) Prior Publication Data

US 2013/0053700 A1    Feb. 28, 2013

Related U.S. Application Data (60) Provisional application No. 61/410,825, filed on Nov. 5, 2010, provisional application No. 61/410,827, filed on Nov. 5, 2010, provisional application No. 61/410,830, filed on Nov. 5, 2010, provisional application No. 61/510,831, filed on Nov. 5, 2010, provisional application No. 61/410,833, filed on Nov. 5, 2010, provisional application No. 61/410,834, filed
(Continued)

(51) Int. Cl.
| | |
|---|---|
| *A61B 5/00* | (2006.01) |
| *A61B 3/117* | (2006.01) |
| *A61B 5/145* | (2006.01) |
| *A61B 5/1455* | (2006.01) |
| *G01N 21/64* | (2006.01) |
| *G01N 21/65* | (2006.01) |

(52) U.S. Cl.
CPC .......... *A61B 3/1173* (2013.01); *A61B 5/0068* (2013.01); *A61B 5/0071* (2013.01); *A61B 5/1455* (2013.01); *A61B 5/14546* (2013.01); *A61B 5/4842* (2013.01); *G01N 21/6486* (2013.01); *G01N 21/65* (2013.01); *G01N 2800/042* (2013.01)

(58) Field of Classification Search
CPC .................................................... A61B 5/0071
USPC ................................................ 600/476, 477
See application file for complete search history.

(56) References Cited

U.S. PATENT DOCUMENTS

| | | |
|---|---|---|
| 3,432,227 A | 3/1969 | Soper |
| 4,685,784 A | 8/1987 | Kirchhuebel |
| (Continued) | | |

FOREIGN PATENT DOCUMENTS

| | | |
|---|---|---|
| EP | 1 913 866 A1 | 4/2008 |
| WO | WO 2005/045393 A2 | 5/2005 |
| (Continued) | | |

OTHER PUBLICATIONS

Bang et al., "Development and Validation of a Patient Self-assessment Score for Diabetes Risk", *Ann Intern Med*, 151:775-783 (2009).

(Continued)

*Primary Examiner* — Rajeev Siripurapu
(74) *Attorney, Agent, or Firm* — Lambert & Associates; Gary E. Lambert; David J. Connaughton, Jr.

(57) ABSTRACT

Methods for spectroscopic analysis of biological tissues to classify an individual as diabetic or non-diabetic, or to determine the probability, progression or level of a disease or medical condition in an individual.

7 Claims, 5 Drawing Sheets

Related U.S. Application Data on Nov. 5, 2010, provisional application No. 61/410,835, filed on Nov. 5, 2010, provisional application No. 61/410,839, filed on Nov. 5, 2010.

(56) References Cited

U.S. PATENT DOCUMENTS

| | | | |
|---|---|---|---|
| 4,848,899 A | 7/1989 | Kobayashi et al. | |
| 4,883,351 A | 11/1989 | Weiss | |
| 4,895,159 A | 1/1990 | Weiss | |
| 5,035,500 A | 7/1991 | Rorabaugh et al. | |
| 5,203,328 A | 4/1993 | Samuels et al. | |
| 5,442,412 A | 8/1995 | Frey et al. | |
| 5,582,168 A | 12/1996 | Samuels et al. | |
| 5,882,301 A | 3/1999 | Yoshida | |
| 5,947,955 A | 9/1999 | Kadambi et al. | |
| 6,004,313 A | 12/1999 | Shmmick et al. | |
| 6,088,606 A | 7/2000 | Ignotz et al. | |
| 6,427,082 B1* | 7/2002 | Nordstrom et al. | 600/476 |
| 6,704,588 B2 | 3/2004 | Ansari et al. | |
| 6,869,427 B1 | 3/2005 | Shokoohi | |
| 7,001,018 B1 | 2/2006 | Martin | |
| 7,043,288 B2* | 5/2006 | Davis et al. | 600/310 |
| 7,139,598 B2* | 11/2006 | Hull et al. | 600/317 |
| 2007/0146635 A1* | 6/2007 | LeBlanc et al. | 351/221 |
| 2007/0243521 A1 | 10/2007 | Zuckerman et al. | |
| 2008/0075335 A1* | 3/2008 | Martin et al. | 382/117 |
| 2009/0143685 A1 | 6/2009 | Hull et al. | |

FOREIGN PATENT DOCUMENTS

| | | |
|---|---|---|
| WO | WO 2006/009906 A2 | 1/2006 |
| WO | 2009/120349 | 10/2009 |
| WO | 2012/061835 | 5/2012 |
| WO | 2012/061836 | 5/2012 |

OTHER PUBLICATIONS

Diabetes Prevention Program Research Group, "Reduction in the Incidence of Type 2 Diabetes With Lifestyle Intervention Or Metformin", *NEJM*, 346(6):393-403 (2002).

ADA Committee Report, "Report of the Expert Committee on the Diagnosis and Classification of Diabetes Mellitus", *Diabetes Care* (2003).

Cornell Chronicle: Diabetes tool screens for disease in adults, from the internet, Dec. 21, 2009 http://www.news.cornell.edu/stories/Dec09/NYCdiabetes.html.

European Search Report Regarding EP 11 83 8960.

* cited by examiner

DEVICE FOR DETECTION OF DIABETES

CROSS-REFERENCE TO RELATED APPLICATIONS

This application is related to, and claims the benefit of, U.S. Provisional Patent Application Nos. 61/410,825, 61/410,827, 61/410,830, 61/410,831, 61/410,833, 61/410,834, 61/410,835, and 61/410,839, each of which was filed on Nov. 5, 2010, and each of which is incorporated herein by reference in its entirety.

Concurrently filed herewith on the same day is a co-pending non-provisional patent application Ser. No. 13/291,072 also claiming the benefit of each of the above-identified U.S. Provisional Patent Applications, entitled, "APPARATUS AND METHOD FOR NONINVASIVELY DETECTING DISEASES THAT AFFECT STRUCTURAL PROPERTIES IN BIOLOGICAL TISSUES," assigned U.S. Pat. No. 8,989,848, and having at least one common inventor. The disclosure of this patent is hereby incorporated by reference in its entirety.

BACKGROUND

Non-invasive devices and methods for detecting disease, such as diabetes, are described. In particular, the exemplary embodiments relate to methods and apparatuses suitable for determining in a mammal the presence, likelihood, and/or progression of diabetes mellitus.

Diabetes mellitus ("diabetes") is a group of metabolic diseases in which a person has high blood sugar (hyperglycemia), either because the body does not produce enough insulin, or because the body's cells do not respond to the insulin that is produced. Diabetes is a disease derived from multiple causative factors and characterized by elevated levels of plasma glucose in the fasting state or after administration of glucose during an oral glucose tolerance test (OGTT). There are two primary forms of diabetes mellitus: (1) insulin dependent or Type 1 diabetes (a.k.a., Juvenile Diabetes, Brittle Diabetes, Insulin Dependent Diabetes Mellitus (IDDM)) and (2) non-insulin-dependent or Type II diabetes (a.k.a., NIDDM). Type 1 diabetes develops most often in young people, but can appear in adults that have the same auto anti body as the Type 1. Type 2 diabetes develops most often in middle aged and older adults, but can appear in young people. This high blood sugar condition produces symptoms of polyuria (frequent urination), polydipsia (increased thirst) or polyphagia (increased hunger). Diabetes is a large and growing problem throughout the world's developed and developing nations. As of now, it has been forecasted that approximately one in 10 U.S. adults have diabetes and according to a Centers for Disease Control and Prevention report, cases of diabetes are projected to double, even triple, by 2050 with as many as one in three having the disease, primarily type 2 diabetes.

Insulin is a hormone produced in the pancreas by β-cells. The function of insulin is to regulate the amount of glucose (sugar) in the blood, which enters cells through receptors that accept insulin and allow glucose to enter. Once inside a cell, glucose can be used as fuel. Excess glucose is stored in the liver and muscles in a form called glycogen. When blood glucose levels are low, the liver releases glycogen to form glucose. Without insulin, glucose has difficulty entering cells. In persons with diabetes mellitus, the pancreas either produces no insulin, too little insulin to control blood sugar, or defective insulin. Without insulin, these symptoms progress to dehydration, resulting in low blood volume, increased pulse rate, and dry, flushed, skin. In addition, ketones accumulate in the blood faster than the body is able to eliminate them through the urine or exhaled breath. Respiration becomes rapid and shallow and breath has a fruity odor. Other symptoms indicating a progression towards diabetic ketoacidotic coma (DKA) include vomiting, stomach pains, and a decreased level of consciousness. Persons with diabetes are at increased risk for debilitating complications such as renal failure, blindness, nerve damage and vascular disease. Although risk for or progression of complications can be reduced through tight glucose control combined with drug therapy and lifestyle changes, effective mitigation of complications begins with early detection. The disease leads to serious complications, including hyperglycemia, macroangiopathy, microangiopathy, neuropathy, nephropathy and retinopathy. As a result, diabetes adversely affects the quality of life. Similarly, uncontrolled Type 2 diabetes leads to excess glucose in the blood, resulting in hyperglycemia, or high blood sugar.

Unfortunately, the diagnosis of diabetes in a person often occurs years after disease onset and after complications are already present. More aggressive screening of individuals at risk for diabetes is needed. Modern diabetes screening and monitoring is a particularly "puncture-intensive" because diabetics have to draw blood to test their glucose levels. The only practical, reliable screening method currently available for monitoring blood glucose is by means of blood sampling. The primary screening and diagnostic tests currently in use—the Fasting Plasma Glucose (FPG) and the Oral Glucose Tolerance Test (OGTT)—are not considered to be optimum because they are inconvenient and unpleasant. Both require venous draws and are fasting tests so they can only be practically administered during morning appointments and are prone to non-compliance issues. For the OGTT, the measurement occurs two (2) hours after the patient ingests a 75 g oral glucose load. Numerous studies have evaluated the performance of each of these tests in diverse populations. It is believed that approximately one-half of those with diabetes are misclassified by a single FPG test. In addition, it is believed that the OGTT suffers from relatively poor reproducibility. In addition, the HbA1c test reflects longer term 90 day glycaemia and control or lack of control than FPG does, the results of the test can also be distorted due to recent changes in diet or hemolytic conditions. Such blood glucose measurement methodologies have limited value as indices of long-term glycemic status. In summary, blood glucose measurements (such as HbA1c and FPG) have limited value as reliable indices of long-term glycemic status.

Consequently, an accurate, reliable and convenient and noninvasive screening test is needed as a viable alternative to current tests. Ideally, an improved screening test would measure an analyte that is directly related to progression of the disease and the risk of complications, and the chemical marker would be invariant to within- or between-day changes in the patient as an integrated biomarker. In addition, the measurement should offer sufficient accuracy to detect diabetes in its early stages and possess adequate precision to eliminate the requirement for repeat, confirmatory testing. Once it becomes apparent that a patient may possibly have diabetes, doctors and health care providers will ask the patient to return for more tests on a periodic basis to determine whether the patient's condition actually develops into the disease. There are certain protocols about how long a patient should wait before being recalled for more testing. If a patient has few symptoms suggestive of diabetes, then the patient may not be recalled for more than a year. If several suggestive symptoms are present, then the patient may be recalled after only a few months. It would be useful if there was available a diagnostic tool and methods for noninvasively and accurately determining whether a patient is at risk of actually developing the diabetes.

A major consequence of hyperglycemia is excessive glycosylation (non-enzymatic glycation) of proteins in a process known as the Maillard reaction. Excessive glycosylation eventually causes the formation of various protein-protein cross-links and non-crosslinked structures called Advanced Glycation End-products (AGEs). AGEs are believed to present an attractive candidate analyte for non-invasive measurements. AGEs have been implicated as causal factors in the complications of diabetes, including diabetic retinopathy (DR). Protein glycation is a multi-stage reaction that begins with formation of a sugar adduct to protein, known as a fructosamine or Amadori compound, which gradually matures to form AGEs. Some AGEs require oxidation chemistry for their formation and are known as glycoxidation products. Collagen is a protein that readily undergoes glycation and glycoxidation. Because of its long half-life, the level of AGEs in collagen is believed to act as a long-term integrator of overall glycemia that is insensitive to short- or intermediate-term fluctuations in glycemic control. Consequently, AGEs accumulate naturally during healthy aging, but at significantly accelerated rates in persons with diabetes. Protein glycation and AGE formation are accompanied by increased free radical activity that contributes to the biomolecular damage in diabetes. Levels of AGEs are positively correlated with the presence of retinopathy, nephropathy and neuropathy and, as such are an indicator of systemic damage to protein in diabetes and a metric of a patient's risk for diabetic complications. In addition, due to the mild to severe hyperglycemia associated with pre-diabetes and type 2 diabetes, individuals who are in the early stages of this continuum will accumulate AGEs at higher than normal rates in their tissues. Thus, given sufficient assay sensitivity, an accurate AGE measurement in an individual offers the promise to detect early departure from normal glycemia. Currently, AGEs are assayed by invasive procedures requiring a biopsy specimen, and consequently are not used in diabetes screening or diagnosis.

Tissue such as the ocular lens can exhibit fluorescence when excited by a light source of a suitable wavelength. This fluorescence emission, arising from endogenous fluorophores, is an intrinsic property of the tissue and is called autofluorescence to be distinguished from fluorescent signals obtained by adding exogenous markers (like sodium fluorescein). The tissue fluorophores absorb certain wavelengths of light (excitation light), and release it again in light of longer wavelengths (emission). Several tissue fluorophores have been identified, such as collagen, elastin, lipofuscin, NADH, porphyrins and tryptophan. Each fluorophore has its characteristic excitation and emission wavelength, that enables localization and further quantification of a particular fluorophore. Autofluorescence can be induced in several tissues and can therefore be applied in investigation of several diseases. It is also used to distinguish malignant from benign tissue in several tissues, such as the skin and cervix. Furthermore, in ophthalmology, autofluorescence of the lens increases with ageing and diabetes. Autofluorescence of the lens appears to be caused by glycation and, subsequent oxidation of lens crystalline, which forms AGEs. The crystalline lens represents an exceptional bio target since the proteins in the lens are relatively static for life and do not turn over (i.e., undergo reverse glycation) allowing for the accumulation of AGEs.

A core technology in noninvasive testing is fluorescence spectroscopy (a.k.a. fluorometry or spectrofluorometry), which is a type of electromagnetic spectroscopy that analyzes fluorescence from a sample by detecting the presence of certain molecules by measuring their reflected or emitted light. It involves using a beam of high energy (short wavelength) light, that excites the electrons in molecules of certain compounds and causes them to emit light (fluorescence) of a lower energy, typically, but not necessarily, visible light. A complementary technique is absorption spectroscopy. In fluorescence spectroscopy, the species is first excited, by absorbing a photon, from its ground electronic state to one of the various vibrational states in the excited electronic state. Collisions with other molecules cause the excited molecule to lose vibrational energy until it reaches the lowest vibrational state of the excited electronic state. The molecule then drops down to one of the various vibrational levels of the ground electronic state again, emitting a photon in the process. As different species of molecules may drop down from different vibrational levels to the ground state, the emitted photons will have different energies, and thus frequencies. Therefore, by analyzing the different frequencies of light emitted in fluorescent spectroscopy, along with their relative intensities, the structure of the different vibrational levels is determined.

Optical spectroscopy offers one potential avenue of early, noninvasive detection of diabetes by quantifying AGEs in the lens of the eye or other tissues. Spectroscopy is the study of light as a function of wavelength that has been emitted, reflected, or scattered from a solid, liquid, or gas. When photons go through a certain material, some are reflected from particle surfaces, some pass through the particles, and some are absorbed. Those photons that are reflected from particles surfaces or refracted through them are called "scattered". Scattered photons may encounter another grain or be scattered away from the surface so they may be detected and measured. Every molecule has a signature structure that reflects light at a specific wavelength; all glucose molecules share a unique signature that's entirely different from other blood components such as hemoglobin. In spectroscopy, a machine fires a laser or other light on the skin or in the eye. If the returning wavelength differs from an established norm, the device alerts the patient or doctor to the presence of the molecule or cell in question. Fluorescence-based systems rely on the propensity of certain cell components, known as fluorophores (e.g., tryptophan, flavins, collagen), to emit light when excited by specific wavelengths of light, with the peak intensity in a different, but corresponding frequency band. The actual amount of light emitted by fluorphores is exceedingly small (on the order of nanowatts) requiring an extremely sensitive photodetection system. The basic function of an optical spectroscopy device is to irradiate the specimen with a desired and specific band of wavelengths, and then to separate the much weaker emitted fluorescence from the excitation light. Only the emission light should reach the eye or detector so that the resulting fluorescent structures are superimposed with high contrast against a very dark (or black) background. The limits of detection are generally governed by the darkness of the background, and the excitation light is typically several hundred thousand to a million times brighter than the emitted fluorescence.

If AGEs are illuminated by light from 300-500 nm, then 400-700 nm fluorescence is emitted. Theoretically, certain early metabolic changes may be detected by fluorescence spectroscopy as AGEs develop. Reflectance techniques attempt to characterize tissue by measuring the amount and wavelengths of light reflected back to a sensitive photodetector when the tissue (e.g., lens of the eye) is exposed to a light source. Fluorescence and reflected light measurements are analyzed using computer-based algorithms; however, these systems have not been studied extensively. Noninvasive ocular fluorescence measurements have been investigated on numerous occasions for diabetes screening and AGE quantitation.

For example, autofluorescence of the lens of the eye can be measured with a computer fluorophotometer (Fluorotron Master, Coherent Radiation Inc. (Palo Alto, Calif.)) fitted with a special lens ("anterior segment adapter") for detailed scanning of lens. Autofluorescence of the lens, excited by a beam of continuous blue light can be scanned along the optical axis by moving the internal lens system of the fluorophotometer by a computer-controlled motor. The wavelengths of excitation and fluorescent light can be set by color filters with peak transmission at 490 nm and 530 nm respectively. The measured autofluorescence, expressed in equivalents of Fluorescein concentration can be recorded as a function of distance in the eye.

It is always desirable to detect diseases early in their progress. In particular, it is desirable to screen and start treating glucose-intolerant individuals as early as possible since, even before the onset of diabetes, vascular lesions gradually develop with deterioration of glucose tolerance. Additionally, beta-cell function is seriously compromised by the time that overt alterations in glucose homeostasis, such as impaired glucose tolerance (IGT) and impaired fasting glucose (IFG), are manifest; thus, timely intervention is important to maintain residual insulin secretory capacity. Early detection enables early treatment which is generally believed to yield a higher success rate in treating various diseases. Recently, it is believed that analyzing eyes, and in particular the lenses of the eyes, can yield indications of various types of diseases. For example, measurements taken of light scattering within the eye has been shown to provide useful diagnostic information to detect and monitor the progress of diseases. Since this region is up to a few millimeters thick, measurements of this region, to be useful, need to be very accurate in the information for the position of the measurement. This is especially true because the human eye is in almost constant motion even when a patient is fixating on an illuminated target. This is particularly true because eye care professionals, such as optometrists, regularly examine, diagnose, treat and manage diseases, injuries, and disorders of the eyes and associated structures, as well as identify related systemic conditions affecting the eye. Optometrists, through their clinical education and experience, and broad geographic distribution, and the means to provide primary eye and vision care for the public. There often the first healthcare practitioners to examine patients with undiagnosed diabetes or ocular manifestations of diabetes.

The effectiveness of early intervention with lifestyle modification or medication in arresting disease progression has been demonstrated by the Diabetes Prevention Program (Diabetes Prevention Program Research Group. NEJM 346: 393-403, 2002). However, the determination of IGT and IFG is itself an issue due to the relatively invasive nature of these assessments, particularly that of IGT by an oral glucose tolerance test (OGTT). In addition, an important additional diagnostic problem is monitoring of glucose homeostasis for confirming diabetes. Compliance with glucose monitoring is poor because of the pain and inconvenience of conventional blood collection using lancets. Furthermore, non-invasive monitoring techniques for diabetes, and to determine the efficacy of therapy, are desirable. Finally, assessment of progression of frank diabetes to complications is only feasible after complications are well established. Thus, it would be beneficial to have methods for assessing the development of diabetes from pre-diabetes, and for monitoring the course of the disease.

Further, there is known at least one attempt to produce a commercial grade non-invasive diabetes detection/screening device that measures crystalline lens fluorescence, known as the Accu-Chek D-Tector. The Accu-Chek-D-Tector is essentially a confocal microscope in that it uses confocal optics to measure AGEs to check for early signs of uncontrollable blood sugar levels and type 2 diabetes because they build up more quickly in the eyes of individuals with high blood sugar levels than in the eyes of individuals with normal levels. The device employs so called biophotonic technology and detects diabetes by shining a blue light into the lens of the eye of a patient. The returned light is collected and analyzed. The light emitted from the eye of a person with diabetes is more intense than that of a person without diabetes. In particular, a laser beam passes through a light source aperture and then is focused by an objective lens into a small (ideally diffraction limited) focal volume within or on the surface of a patient's eye. Scattered and reflected laser light as well as any fluorescent light from the illuminated spot is then re-collected by the objective lens (collector). A beam splitter separates off some portion of the light into a detection apparatus, which in fluorescence confocal microscopy may have a filter that selectively passes the fluorescent wavelengths while blocking the original excitation wavelength. After optionally passing through a pinhole, the light intensity is detected by a photodetection device (e.g., a photomultiplier tube (PMT)), transforming the light signal into an electrical one that is recorded by a computer for further analysis. In particular, the Accu-Chek D-Tector shines a blue light into the lens of the eye, then collects and analyzes the returned light.

However, major drawbacks of the Accu-Chek-D-Tector are that it is relatively slow, imprecise and costly to manufacture. Although the device could purportedly take readings in 30 seconds (15 seconds for fluorescence, 15 seconds for backscatter) to obtain a ratio of fluorescence signal to backscattered signal from a specific location within the patient's lens, the device employed a sliding filter changer to select either green (fluorescence) or blue (backscattered) light striking a photodetector via a crank mechanism. Rotation of a step motor actuated the two position slider taking one or more seconds to move from one filter to the other. In addition, in use, a patient to self-align to the device via a fixation system that made it difficult and time-consuming.

Most non-invasive analyzers are not designed specifically for high-throughput screening purposes. They are difficult and expensive to integrate into a high-throughput screening environment. Even after the analyzer is integrated into the high-throughput screening environment, there often are many problems, including increased probability of system failures, loss of data, time delays, and loss of costly compounds and reagents. Thus, prior non-invasive diabetes detection devices generally have not recognized the need to provide analytic flexibility and high performance.

A real need exists for a versatile, sensitive, high-throughput screening apparatus and methods that can handle multiple detections and wide ranges of patients while reliably maintaining a high level of sensitivity. In addition to early identification, if there is a need for diabetes detection apparatus, devices, methods and/or systems for detecting diabetes that requires no fasting and is a cumulative test that is not exposed to variations in glucose levels caused from a variety of reasons, including food, stress certain drugs, or short term changes in diet and exercise.

BRIEF DESCRIPTION OF THE DRAWINGS

The accompanying drawings, which are incorporated in and constitute a part of the specification and written description, illustrate exemplary embodiments and, together with the written description, serve to exemplify principles of the claims.

DESCRIPTION OF EXEMPLARY EMBODIMENTS

Various exemplary embodiments of an invention are now described with or without reference to a Figure, where like reference numbers indicate identical or functionally similar elements. The example embodiments, as generally described and illustrated in the Figures herein, could be arranged and designed in a wide variety of different configurations. Thus, the following more detailed description of exemplary embodiments, as described and/or represented in the Figures, is not intended to limit the scope of the subject matter claimed, but is merely representative of the exemplary/example embodiments.

Certain aspects, advantages, and novel features are shown in the Figures and/or described herein. It is to be understood that not necessarily all such aspects, advantages, and features expressly or inherently discussed herein may or may not be employed and/or achieved in accordance with any particular embodiment or aspect thereof. Thus, for example, those skilled in the art will recognize that an exemplary embodiment may be carried out in a manner that achieves one advantage or group of advantages as taught or inferred herein without necessarily achieving other advantages as may be taught or suggested herein. Of course, advantages not expressly taught or inferred herein may be realized in one or more exemplary embodiments.

Except as otherwise expressly provided, the following rules of interpretation apply to this specification (written description, claims and drawings): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (c) descriptive headings are for convenience only and shall not control or affect the meaning or construction of any part of the specification; and (d) "or" and "any" are not exclusive and "include" and "including" are not limiting. Further, The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the preferred methods and materials are now described.

As used herein, the terms "an embodiment", "embodiment", "embodiments", "the embodiment", "the embodiments", "one or more embodiments", "some embodiments", "certain embodiments", "one embodiment", "another embodiment" and the like mean "one or more (but not necessarily all) embodiments of the disclosed apparatus and/or method", unless expressly specified otherwise.

The term "determining" (and grammatical variants thereof) is used in an extremely broad sense. The term "determining" encompasses a wide variety of actions and therefore "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The word "exemplary" or "example" is exclusively used herein to mean "serving as an example, instance, or illustration." Any embodiment described herein as "exemplary" or "example" is not necessarily to be construed as preferred or advantageous over other embodiments.

As used herein the terms "user" or "patient" or "subject" may be used interchangeably, and the foregoing terms comprise without limitation human beings, whether or not under the care of a physician, and other mammals. The terms "eye scan," "scanning the eye," or "scan the eyes," as used herein, are broad interchangeable terms that generally refer to the measurement of any part, substantially all, or all of the eye, including but not limited to the eye lens or any other tissue or nerve related to the eye.

The embedded computer subsystem can include at least one central processing unit (CPU) or "processor", memory, storage, a display and a communication link. An example of a CPU is the Intel Pentium microprocessor. The memory can be, for example, static random access memory (RAM) and/or dynamic random access memory. The storage can be accomplished with non-volatile RAM or a disk drive. A liquid crystal display is an example of the type of display that would be used in the device. The communication link can be a high speed serial link, an ethernet link or a wireless ("WiFi" or "broadband") communication link. The embedded computer subsystem can produce disease state predictions from received and processed data, perform calibration maintenance, perform calibration transfer, run instrument diagnostics, store a history of past analysis and other pertinent information, and in some embodiments, can communicate with remote hosts to send and receive data and new software updates.

"Software" and "Machine-readable code operable on an electronic computer" are synonymous and refers to software or hard-wired instructions used to control the logic operations of the computer. The term computer or processor refers to an electronic computer or its specific logic-processing hardware. The machine-readable code is embodied in a tangible medium, such as a hard disc or hard-wired instructions.

Figure 3A:
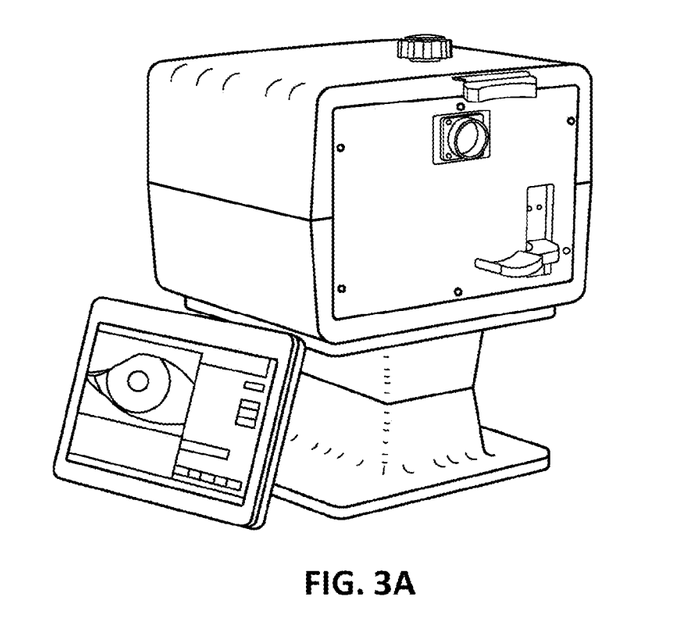
FIGS. 3A and 3B depict perspective and front views, respectively, of an example embodiment showing external parts.
Figure 3B:
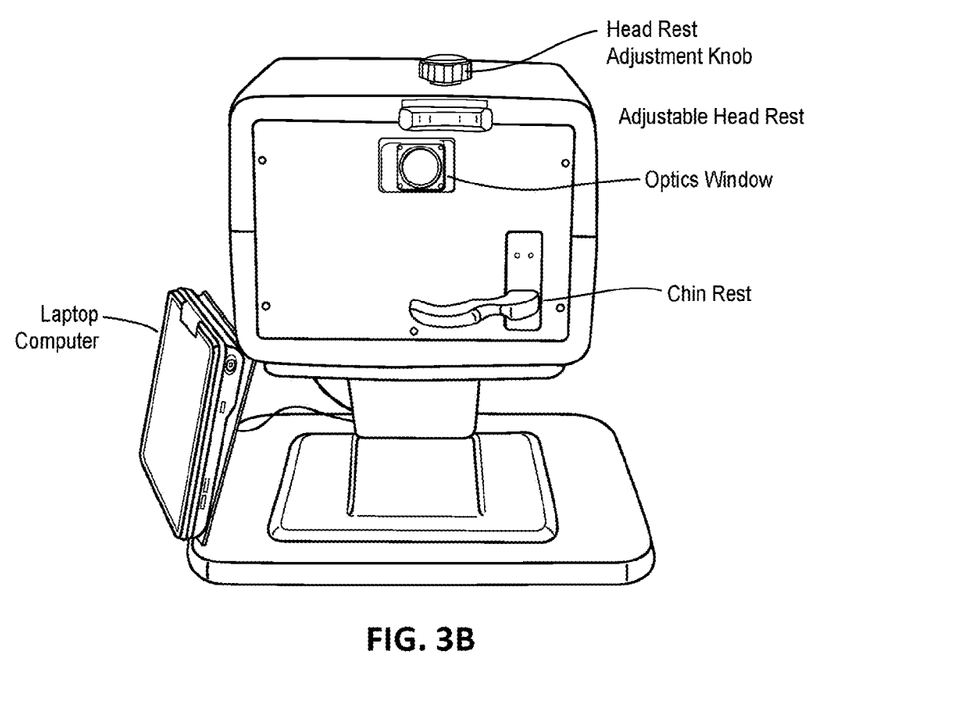

The processor in the system may be a conventional microcomputer having keyboard and mouse input devices, a monitor screen output device, and a computer interface that operably connects various components of the system, for example, including an eye tracking assembly or device, robotic elements, etc. (see example embodiments depicted in FIGS. 3A and 3B.)

It is to be further understood that all measurement values are approximate, and are provided for description. Although methods and materials similar or equivalent to those described herein can be used in the practice or testing of this disclosure, suitable methods and materials are described below. All publications, patent applications, patents, and other references mentioned herein are incorporated by reference in their entirety. In case of conflict, the present specification, including explanations of terms, will control. In addition, the materials, methods, and/or examples are illustrative only and not intended to be limiting.

Some features of the embodiments disclosed herein may be implemented as computer software, electronic hardware, or combinations of both. To illustrate this interchangeability of hardware and software, various components may be described generally in terms of their functionality. Whether such functionality is implemented as hardware or software depends upon the particular application and design constraints imposed on the overall system, as readily obtainable by a skilled person. Skilled persons may implement the described functionality in varying ways for each particular application, but such implementation decisions should not be interpreted as causing a departure from the scope of the claims.

Where a described functionality is implemented as computer software, such software may include any type of computer instruction or computer executable code or algorithm located or stored (even temporarily) within a memory device and/or transmitted as electronic signals over a system bus or network. Software that implements the functionality associated with components described herein may comprise a single instruction, or many instructions, and may be distributed over several different code segments, among different programs, and across several memory devices.

The herein described embodiments constitute an improvement of one or more of the methods and apparatuses (purportedly depicting the above-mentioned Accu-Chek D-Tector design) disclosed in the following patents, the entire disclosures (written description and drawings) of each are incorporated herein by reference:

U.S. Pat. No. 5,203,328 to Samuels entitled, "Apparatus And Methods For Quantitatively Measuring Molecular Changes In The Ocular Lens." This patent discloses an apparatus and method for determining whether a patient has diabetes. The system and method measure characteristics of the patient's eye that are indicative of diabetes. Specifically, the system and methods illuminate ocular tissue in a patient's eye, and measure backscattered light and fluorescent radiation generated by the ocular tissue in response to the excitation light. The intensity of the backscattered light and fluorescent light at particular wavelengths are then used to determine whether the patient has diabetes.

U.S. Pat. No. 5,582,168 entitled, "Apparatus And Methods For Measuring Characteristics Of Biological Tissues And Similar Materials." This patent exemplifies apparatuses and methods that combine two or more measurement techniques to arrive at a more accurate ultimate determination by measuring characteristics of biological tissues and similar materials. These apparatus and methods are described with respect to measurements of the human eye. In addition, the correction methodologies described therein involve measurements of elastically scattered excitation light. Samuels describes a simple linear correction technique.

U.S. Pat. No. 6,088,606 entitled, "Method and apparatus for determining a duration of a medical condition." This patent discloses a system and method for determining the duration of a medical condition and methods relating to determining the duration of a disease, not for diagnosing or screening for the presence of disease or for quantifying the concentration of specified chemical analytes.

U.S. Pat. No. 4,895,159 entitled, "Diabetes Detection Method," and U.S. Pat. No. 4,883,351 entitled, "Apparatus for the Detection of Diabetes and Other Abnormalities Affecting the Lens of the Eye," each disclose systems and methods for detecting the existence of diabetes using only backscattered light.

Figure 1:
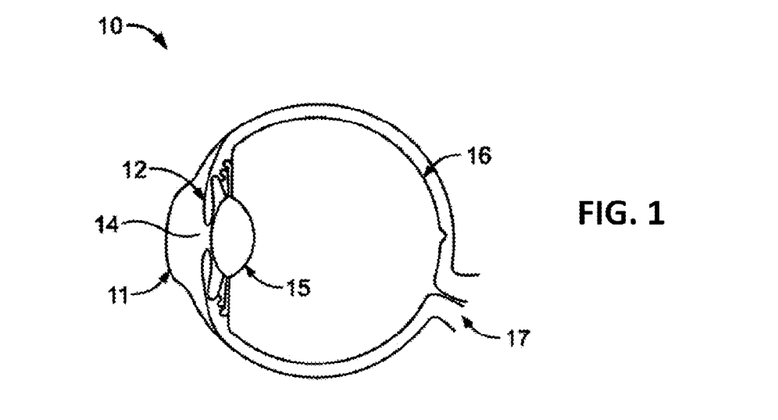
FIG. 1 shows a side view cross-section of an eye and its constituent parts.

FIG. 1 shows a side-view of an eye 10. Eye 10 includes a cornea 11, an iris 12, a pupil 14, a lens 15, a retina 16 and optic nerve 17. Light enters the eye through pupil 14, is focused and inverted by cornea 11 and lens 15, and is projected onto retina 16 at the back of the eye. Iris 12 acts as a shutter that can be opened or closed to regulate the amount of light entering the eye via pupil 14.

In a further example embodiment, an excitation light source (e.g., blue LED) may be used to illuminate a specific point in the lens of a subject's eye that is approximately 50% to 80% (optionally, 60% to 75%) and all subranges therebetween, from the front edge of the inferior quadrant of the subject's lens. It has been determined that measurements at this location in the mammalian eye provide consistent measurements without undesirable delays or interference that can skew data collection. For example, care should be taken in fluorescence spectroscopy to avoid confounding influences of unwanted optical signals in the detection of the compound of interest (e.g., AGEs). There may be potentially confounding influences from macular pigments, cataracts, fluorescence emissions from areas other than the lens, etc. The influence from these and other factors may be reduced by choosing an excitation wavelength that is just outside the absorption of the undesirable influence but still overlapping the AGEs absorption on its long-wavelength shoulder, in the green wavelength region. As such, measurements taken from inferior position, as mentioned above, are advantageous because interferences are minimized.

Eye 10 consists of four quadrants in relation to the optic nerve head: (a) a temporal portion, which consists of the quadrant towards the temple of the skull, (b) a superior portion, which consists of the quadrant above the optic nerve head, (c) a nasal portion, which consists of the quadrant towards the nose, and (d) an inferior portion, which consists of the quadrant below the optic nerve head. In one aspect, measurements of a particular quadrant or quadrants of the ocular lens, i.e., temporal, superior, nasal, and/or inferior, can be collected/used to generate data on the structural features of the eye. In other words, in a example method for optical detection of AGE's in the lens of a subject's eye, the subject's eye may be exposed to a fixation point. Exposing the subject's eye to an excitation light source may comprise directing the light to a desired portion of the subject's eye. Directing the light to a desired portion of the subject's eye may comprise directing the light to a nasal portion, a temporal portion, a superior portion or an inferior portion of the lens. It may also comprise directing the light to other parts or tissues of the eye, such as, without limitation, the retina, the vitreous, the corona, etc.

Example embodiments comprise an apparatus and method suitable for determining properties of in vivo tissue from spectral information collected from the lens of the eye. In general, an illumination system provides light at one or more wavelength ranges, which are communicated to an optical collection device. Light homogenizers and mode scramblers can be employed to improve the performance in some embodiments. The optical system is non-invasive and does not physically contact the eye. The optical source essentially receives light from the illumination system and transmits it to the lens of the eye. The optical collection system receives light emitted from the eye lens tissue by fluorescence thereof in response to the light. The optical collection device can communicate the light to a spectrograph which produces a signal representative of the spectral properties of the light. An analysis system (computer) determines a property of the eye lens from the spectral properties.

In a further example embodiment, a method for determining a measure of a tissue state (e.g., glycation endproduct or disease state) in an individual is provided. A portion of the tissue of the individual is illuminated with excitation light, and then light emitted by the tissue due to fluorescence of a chemical in the tissue responsive to the excitation light is detected. The detected light can be combined with a model relating fluorescence with a measure of tissue state to determine a tissue state. The example embodiment can comprise single wavelength excitation light, scanning of excitation light (illuminating the tissue at a plurality of wavelengths), detection at a single wavelength, scanning of detection wavelengths (detecting emitted light at a plurality of wavelengths), and combinations thereof. Also provided are correction techniques that reduce determination errors due to detection of light other than that from fluorescence of a chemical in the tissue. For example, the reflectance of the tissue can lead to errors if appropriate correction is not employed. The embodiment can also comprise a variety of models relating fluorescence to a measure of tissue state, including a variety of methods for generating such models. Other biologic information can be used in combination with the fluorescence properties to aid in the determination of a measure of tissue state. The embodiment also comprises apparatuses suitable for carrying out the method, including appropriate light sources, detectors, and models (for example, implemented on computers) used to relate detected fluorescence and a measure of tissue state. For example, the emitted light may include wavelengths of about 200 nm to about 250 nm; about 400 nm to about 450 nm, about 450 nm to about 500 nm, about 500 nm to about 550 nm, about 600 nm to about 650 nm, about 650 nm to about 700 nm, about 700 nm to about 750 nm, and combinations thereof, and all subranges therebetween each of the above-identified ranges.

Figure 2:
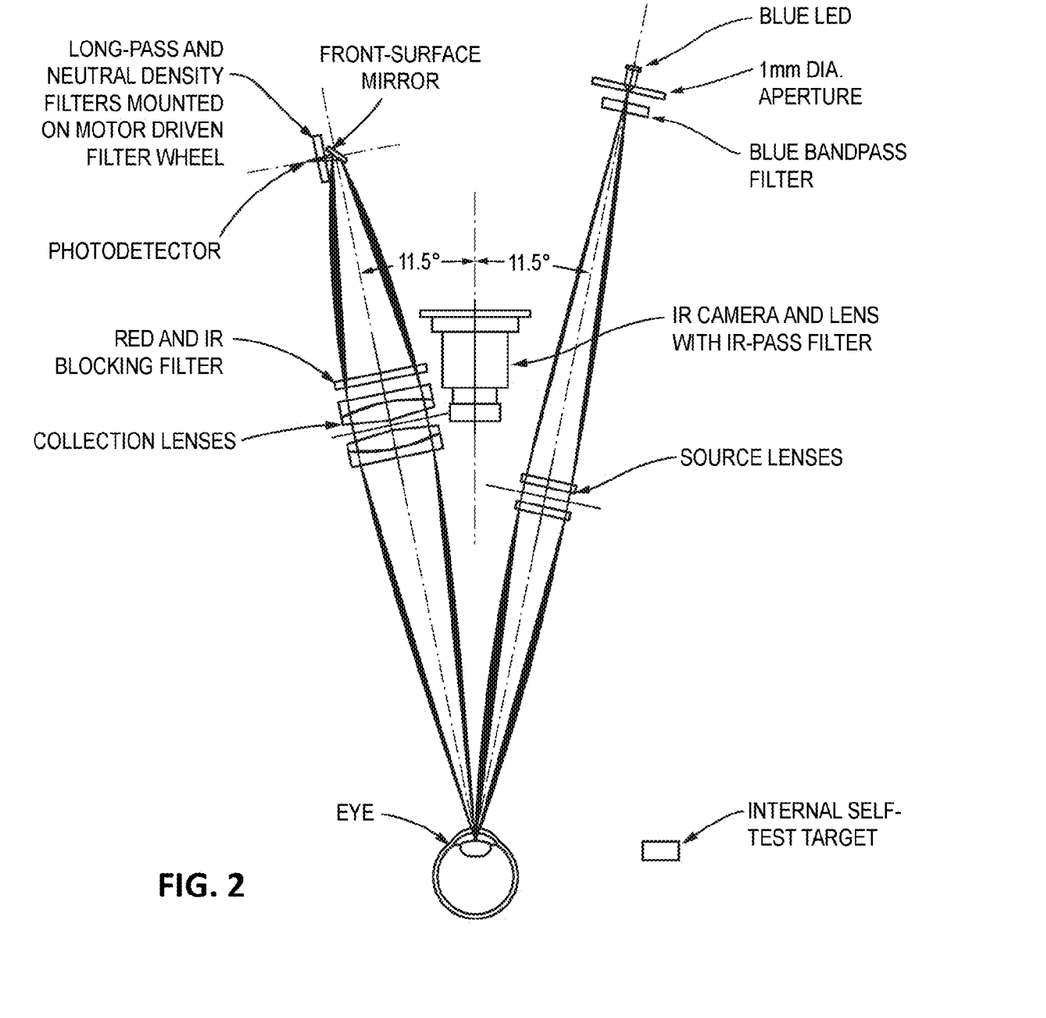
FIG. 2 depicts a schematic view of an example embodiment of an LED light optics source assembly.

FIG. 2 is a schematic depicting an example embodiment of an apparatus comprising a confocal setup (it will be noted that unlike previous apparatuses, the light path does not encounter any beam splitters or dichroic mirrors, thereby increasing energy of the light transmission). In specific embodiments, the returned light can include fluorescent light generated by the target tissue in response to the excitation light. The intensity of the returned fluorescent light can be compared to a chronologically age-related expected intensity of fluorescent light for individuals that do not have diabetes. Optionally, an amount that the intensity of the actual returned fluorescent light exceeds an expected intensity for returned fluorescent light can then be used to determine at least whether or not an the individual has been experiencing a medical condition, e.g., diabetes, (i.e., overt diabetes, pre-diabetes, gestational diabetes, etc.), an eye condition caused by diabetes, retinopathy, retinal vascular occlusion, vitreoretinopathy, age-related macular degeneration, inherited retinal degeneration, pseudotumor cerebri, glaucoma, cataracts, etc.

In an example embodiment, the returned light can include fluorescent light generated by the AGEs in the lens of the eye. The intensity of the returned fluorescent light can be compared to a chronologically age-related expected intensity of fluorescent light for individuals that do not have diabetes. Optionally, an amount that the intensity of the actual returned fluorescent light exceeds an expected intensity for returned fluorescent light can then be used to determine whether the individual has been experiencing a medical condition. The temporal characteristics of the fluorescent light, instead of intensity, can also be detected and used to determine how long the patient has been experiencing a medical condition. The temporal characteristics can be analyzed by any suitable technique including, without limitation, directly measuring the decay time of the fluorescent emissions, by phase shift techniques, by polarization anisotropy techniques, or by any other method of detecting temporal characteristics of the fluorescent light.

In still other example embodiments, the returned light can include backscattered excitation light that returns from the target tissue. Such embodiments may utilize the backscattered light alone to make a determination, or the backscattered light could be used in conjunction with fluorescent light generated by the target tissue to arrive at a determination. In some embodiments, a light source for providing excitation light, and a detector for detecting returned light are arranged as a confocal system. As previously discussed, such a confocal system allows one to interrogate small volumes of target tissue within a larger volume of tissue. Confocal systems allow measurements to be conducted on volumes of tissue that are below the surface of a target tissue. Also, patient specific information could also be taken into account by an example system or method. For instance, a patient's age, sex, and physical characteristics could also be used, in addition to optical information, to determine how long a patient has been experiencing a medical condition. This would allow the system or method to account for age varying characteristics such as fluorescent intensity.

In an example embodiment, the excitation light source comprises a blue light emitting diode (blue LED) to illuminate a point in the lens of a patient's eye approximately 50% to 80%, optionally, 60% to 75% inferior from the front edge of the crystalline eye lens. In this embodiment, a blue LED light source produces excitation light coupled to one or more optical bandpass filters to produce excitation light having a desired wavelength optionally coupled with frequency altering device that may be a non-linear frequency doubling device, or any other device capable of changing the frequency of the light produced by the blue LED light source so that light having a desired wavelength is generated. The excitation radiation in the appropriate wavelength band is then directed through an optical delivery system which focuses the excitation light onto a target tissue in the eye of a patient. Return light, which can include a backscattered portion of the excitation light and/or fluorescent light produced in response to the excitation light, is then collected by a photo detector for analysis. One or more excitation wavelengths may be used and one or more fluorescence wavelengths may be collected.

In a further example embodiment, provided herein is a system and method for determining whether a patient has been experiencing a medical condition by comparing characteristics of fluorescent emissions from a target tissue to expected characteristics. For example, a target tissue is illuminated with excitation light, and fluorescent emissions generated by the target tissue in response to the excitation light are detected. Different characteristics of the fluorescent emissions, including the fluorescent emission intensity or the fluorescent lifetime may be determined. The determined characteristics of the detected fluorescent emissions are then compared to expected characteristics of the fluorescent emissions or other factors. In some instances, the backscattered portions of the excitation light may also be used to make the determination which may provide a more accurate measurement result, the intensity of the fluorescent light is normalized, using backscattered excitation light, to account for a variety of factors. Such factors could include variations in the opacity of the target tissue, which can vary with a patient's age or physical condition.

In such a system, a detector would be capable of determining an intensity of the fluorescent light generated by the target tissue, as well as an intensity of excitation light that is backscattered from a patient's eye. Because the fluorescent light will usually have a different wavelength than the backscattered excitation radiation, the detector can be configured to detect the intensity of light returned from the target tissue at the different respective wavelengths for the excitation light and the fluorescent light. A ratio of the fluorescent light intensity to the intensity of the backscattered excitation light is then determined, thereby normalizing the peak intensity of the fluorescent component. The normalized fluorescent intensity is then compared to an expected normalized fluorescent intensity to determine the duration that the patient has been experiencing a medical condition.

Variations in the opacity or transmissivity of the target tissue (e.g., lens of a patient's eye) or optical coupling (variations in beam orientation to the eye surface) can affect the amount of excitation light that is actually delivered to the target tissue, and the amount of fluorescent light that escapes the target tissue and is detected by the detector. Normalizing the fluorescent light with the backscattered light creates a measure of the fluorescent light that automatically accounts for variations in the amount of excitation light energy actually delivered to the target tissue, and variations in the amount of fluorescent light that escapes the patient's eye after the fluorescent light is generated. In a particular example embodiment, where the intensity of fluorescent light returned from the target tissue is normalized, the Rayleigh/Mie component of the backscattered excitation light is used for the normalization, so FL Ratio=F (Fluorescence Signal)/S (Scattered Signal). Additionally the fluorescent light can be also normalized by the total returned signal which is Scatter+Fluorescence. So in that case FL ratio=F/(S+F).

Figure 4:
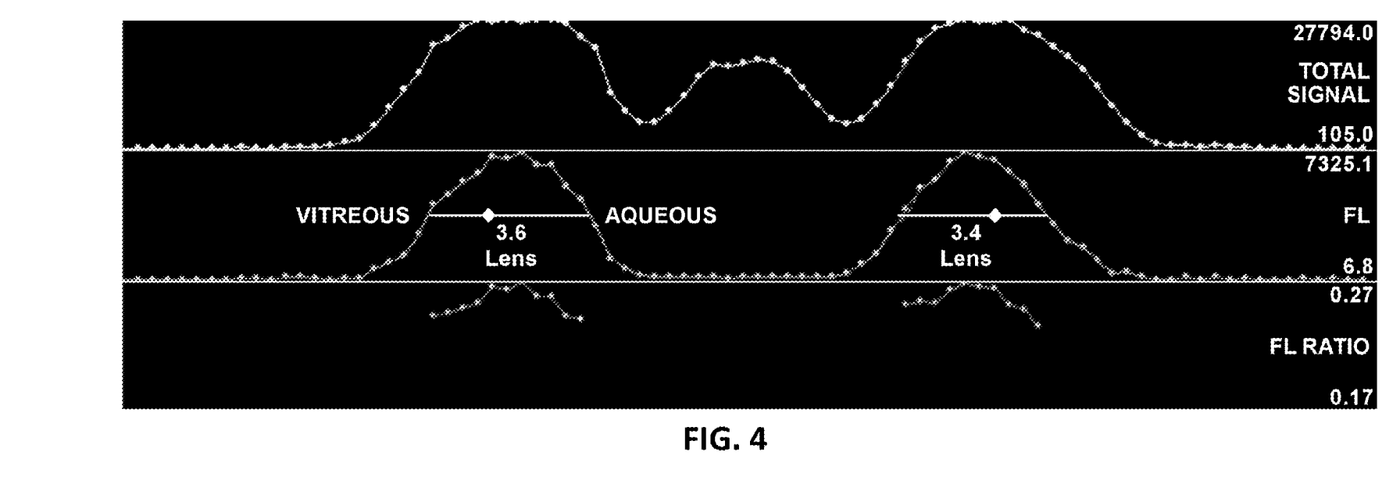
FIGS. 4 and 6 depict scan results of an eye using an example embodiment.

If two or more scans are taken thru the lens; a quality checking algorithm can compare multiple scans to insure consistent fluorescence, scatter and bandwidth. See FIG. 4. If two successive scans were required to be within a certain amount (20% for example) and the results averaged. The net effect would be to improve device precision. So by adjusting this consistency threshold the device precision can be improved increasing the true positive and true negative reporting rate. In addition, a single scan or multiple scans can be compared for lens thickness, pupil diameter to the normal range found in humans are rejected if outside the normal range.

Figure 5:
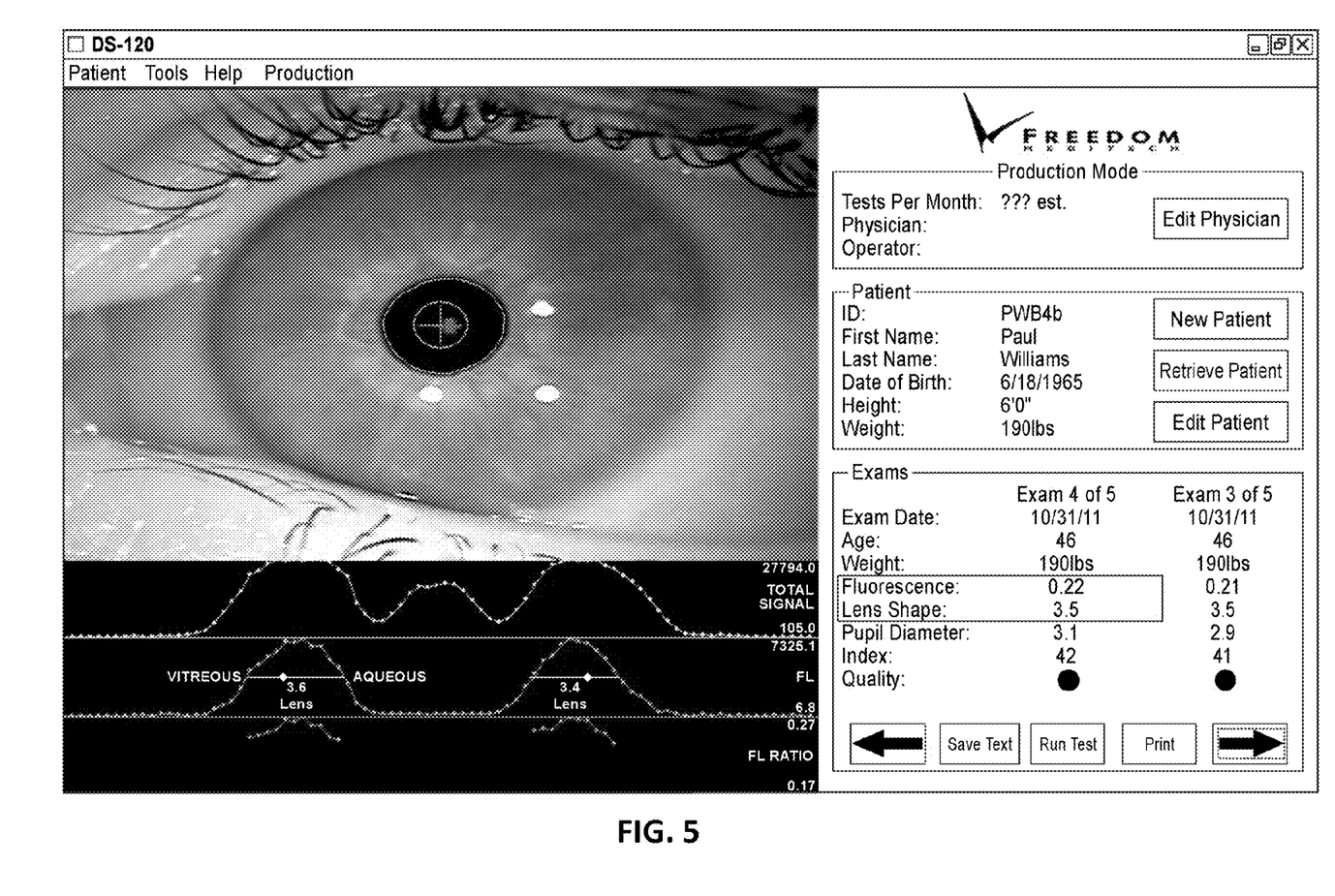
FIG. 5 depicts an example embodiment of a pupil self-alignment system

To align the excitation and emission optics to the eye for a scan the device must first self align to the pupil. A video camera is used to locate the subject's pupil (FIG. 5). An algorithm creates a circle representing the pupil. That circle is checked against normal ranges for the human pupil diameter. And the center of the pupil is computed, the optics automatically re-align to this computed center. And that pupil center is tracked for movement during the scan. Additionally, the scan thru the lens can be offset from the center of the pupil to compensate for clipping of the signal from the Iris.

Eye motion during a scan can also affect device performance and precision. So tracking the pupil location during a scan can be used as a quality metric to reject scans (see purple color and marks on pupil in FIG. 5).

Figure 6:
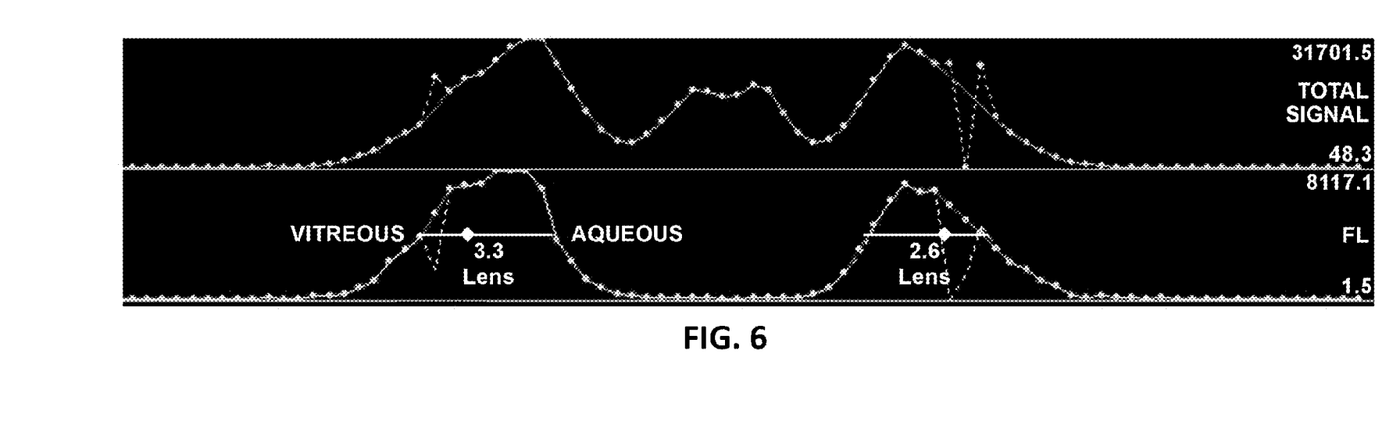
Figure 7:
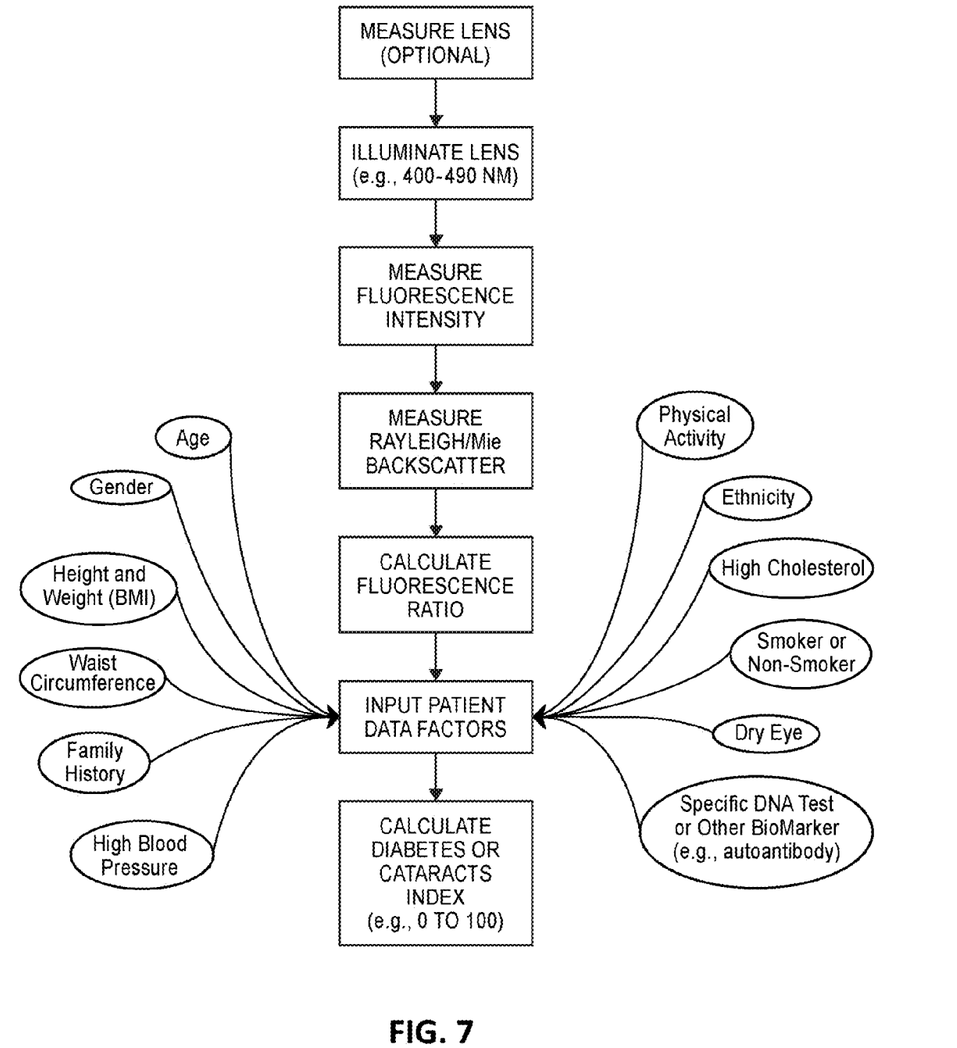
FIG. 7 is a flow chart showing alternative steps of a method embodying an example embodiment.

The scan thru the lens should have a smooth parabolic shape. Transients faster than the sample volume speed thru the lens can be rejected or smoothed (FIG. 6). So for example if the sample volume were 1 mm long and 2 points within a scan were 0.5 mm apart we would expect the signal level could only change 1 mm/2 mm or 50% of the maximum value of that scan. If the transient were larger the erroneous point could be skipped and interpolated around, or the entire scan rejected.

The duration that a patient has been experiencing a medical condition may be determined based on the results of the comparison. The characteristics of the fluorescent emissions that are detected and compared can be the intensity of the fluorescent emissions, the lifetime of the fluorescent emissions, or other characteristics of the fluorescent emissions that are indicative of duration that a patient has been experiencing a medical condition.

Also disclosed is an algorithm for determining the disease state of an individual by measuring ocular tissue using Fluorescence at one or more wavelengths and Rayleigh/Mie back scatter spectroscopy techniques, optionally in combination, with one or more coefficients or factors selected from the group consisting of, without limitation, age, gender, height, weight, body mass index (BMI), waist circumference, HbA1c, biomarkers (e.g., auto antibody), ethnicity, smoking, physical activity, high blood pressure, high cholesterol, dry eye, family history of diabetes, cataracts or other diseases. The lens measurements and biomarkers are combined to report a diabetes index a cataracts index or other disease indices. Those factors can be determined by multiple linear regression, Partial Least Squares, or iteratively as node in a neural network or any other suitable methods. Some bio-markers may be a weighted binary term (Smoker/non-smoker). Some may be linear or non-linear effects (Age, BMI). By including these other bio-markers the rate of true positive and true negative can be improved leading to better patent care and earlier diagnosis of disease Suitable biomarkers include, but are not limited to, any member of the group consisting of flavoprotein, bacteria, fungi, yeast, spores, virus, microbes, parasites, connective tissues, tissue components, exudates, pH, blood vessels, reduced nicotinamide adenine dinucleotide (NADH), falvin adenine dinucleotide (FAD), microorganisms, vascular endothelial growth factor (VEGF), endothelial growth factor (EGF), epithelial growth factor, epithelial cell membrane antigen (ECMA), hypoxia inducible factor (HIF-I), carbonic anhydrase IX (CAIX), laminin, fibrin, fibronectin, fibroblast growth factor, transforming growth factors (TGF), fibroblast activation protein (FAP), tissue inhibitors of metalloproteinases (TIMPs), nitric oxide synthase (NOS), inducible and endothelial NOS, lysosomes in cells, macrophages, neutrophils, lymphocytes, hepatocyte growth factor (HGF), anti-neuropeptides, neutral endopeptidase (NEP), granulocyte-macrophage colony stimulating factor (GM-CSF), neutrophil elastases, cathepsins, arginases, fibroblasts, endothelial cells and keratinocytes, keratinocyte growth factor (KGF), macrophage inflammatory protein-2 (MIP-2), macrophage inflammatory protein-2 (MIP-2), and macrophage chemoattractant protein-1 (MCP-I), polymorphonuclear neutrophils (PMN), macrophages, myofibroblasts, interleukin-1 (IL-I), tumour necrosis factor (TNF), nitric oxide (NO), c-myc, beta-catenin, endothelial progenitor cells (EPCs), matrix metalloproteinases (MMPs) and MMP inhibitors. In an example embodiment, memory may be included for recording fluorescence data of the at least one biomarker, or further comprising a processor for comparing the fluorescence spectrum of the at least one biomarker with a predetermined look-up table of fluorescence spectra of biomarkers.

An algorithm stored in an embedded computer subsystem can then be applied to determine likelihood or presence of a disease state. After generating a disease state prediction, the embedded computer subsystem will report a predicted value to the subject. Optionally, the embedded computer subsystem can report the level of confidence in the goodness of the predicted value. If the confidence level is low, the embedded computer subsystem can withhold the predicted disease state and ask the subject to retest. The classification can be reported visually on a display, by audio and/or by printed means. Additionally, the predicted disease state can be stored in memory in order to form a historical record of the analysis.

The embedded computer subsystem can include at least one central processing unit (CPU) or "processor", memory, storage, a display and a communication link. An example of a CPU is the Intel Pentium microprocessor. The memory can be, for example, static random access memory (RAM) and/or dynamic random access memory. The storage can be accomplished with non-volatile RAM or a disk drive. A liquid crystal display is an example of the type of display that would be used in the device. The communication link can be a high speed serial link, an Ethernet link or a wireless communication link. The embedded computer subsystem can produce disease state predictions from the received and processed interferograms, perform calibration maintenance, perform calibration transfer, run instrument diagnostics, store a history of past analysis and other pertinent information, and in some embodiments, can communicate with remote hosts to send and receive data and new software updates.

The embedded computer system can also contain a communication link that allows transfer of the subject's prediction records and the corresponding spectra to an external database. In addition, the communication link can be used to download new software to the embedded computer, update the multivariate calibration model, provide information to the subject to enhance the management of their disease, etc. The embedded computer system is very much like an information appliance. Examples of information appliances include personal digital assistants, web-enabled cellular phones and handheld computers. The communication link can be used for medical billing based on the number of test performed on each device. It can also be used for customer service to track failure or error rates on each device.

In a further example embodiment, a biomicroscope apparatus may be configured with, connected to or in communication with a system for automatically, remotely monitoring the operational status of one or more biomicroscopes disclosed herein each having a computer therein for determining device status information (e.g., usage counts, accounting/billing for usage, accounting/billing for usage over contract minimums, hardware or software error codes, storage or database operations to the point of failure for remote system diagnostics, capturing services response time until performance is restored, etc.) comprising an interference in the biomicroscope to intercept and pass status information from the computer to an interface for capturing and communicating the status information to a remote location, communication link between the interface for capturing and communicating information and the remote location, and a computer at the remote location to process the information. The system utilizes a scanner to poll the biomicroscope. The scanner, in cooperation with the central computer, can poll and monitor each of the biomicroscopes at a uniform rate or, when requested by the user at a central location, vary the poll rate of one or more of the biomicroscopes to poll the selected biomicroscope with increased regularity, slowing the polling rate of the other biomicroscopes, to provide a real-time monitoring of selected biomicroscopes. Depending on the results of a scan or poll sequence, the system may be configured to provide sound and voice capabilities so that the operator is afforded the option to communicate "live" with a customer service representative of a vendor or manufacturer of the biomicroscope to troubleshoot problems. The system is configured to utilize centralized computing and routing and or "cloud" computing or storage.

As used herein, "determining a disease state" includes determining the presence or likelihood of diabetes; the degree of progression of diabetes; a change in the presence, likelihood, or progression of diabetes; a probability of having, not having, developing, or not developing diabetes; the presence, absence, progression, or likelihood of complications from diabetes.

"Diabetes" includes a number of blood glucose regulation conditions, including Type I, Type II, and gestational diabetes, other types of diabetes as recognized by the American Diabetes Association (See ADA Committee Report, Diabetes Care, 2003) and similar governing bodies, hyperglycemia, impaired fasting glucose, impaired glucose tolerance, and pre-diabetes. Ocular tissue reflectance characteristic includes any reflectance property of tissue that is useful in correction of detected light found useful for estimating the tissue's intrinsic Fluorescence and Raleigh scattering spectrum.

A "measure of chemical change due to glycemic control" means any change in the chemical characteristics of tissue that is due to glycemic control, examples including concentration, measurements of the presence, concentration, or change in concentration of glycation end-products in the ocular tissue; measurements of the rate or change in the rate of the accumulation of such end-products;

A "measure of glycation end-product" means any measure of the presence, time, extent, or state of ocular tissue associated with hyperglycemia, including, as examples, measurements of the presence, concentration, or change in concentration of glycation end-products in tissue; measurements of the rate or change in the rate of the accumulation of such end-products; measurements of the presence, intensity, or change in intensity of Fluorescence and the Raleigh back scatter alone or in combination known to be associated with tissue glycation end-products; and measurements of the rate or change in the rate of the accumulation of such signal. When light is described as having a "single wavelength," it is understood that the light can actually comprise light at a plurality of wavelengths, but that a significant portion of the energy in the light is transmitted at a single wavelength or at a range of wavelengths near a single wavelength.

Advantages of the example embodiments may be realized and attained by means of the instrumentalities and combinations particularly pointed out in this written description. It is to be understood that the foregoing general description and the following detailed description are exemplary and explanatory only and are not restrictive of the claims.

While example embodiments have been described in detail, the foregoing description is in all aspects illustrative and not restrictive. It is understood that numerous other modifications and variations can be devised without departing from the scope of the example embodiment.

While the example embodiments have been described in connection with what is presently considered to be practical for intended purposes, it is to be understood that the descriptions are not to be limited to the particular disclosed embodiments, but on the contrary, is intended to cover various modifications and equivalent arrangements included within the spirit and scope of the example embodiment. Those skilled in the art will recognize, or be able to ascertain using no more than routine experimentation, many equivalents to the specific Example embodiments specifically described herein. Such equivalents are intended to be encompassed in the scope of the claims, if appended hereto or subsequently filed.

What is claimed is:

1. A method of determining diabetes connected to the formation of Advanced Glycation End-products (AGEs) in the eye in a subject without need for subject fasting or adjustment for transient variations in subject glucose levels, comprising the steps of:
   (1) locating the subject's pupil with a video camera, creating a circle representing the pupil and comparing its diameter against normal ranges for human pupils, computing the location of the center of the subject's pupil and auto-aligning an optical light source comprising blue light in a confocal biomicroscope to the pupil's center;
   (2) illuminating a point on a crystalline lens of the subject's eye 50 to 80% inferior from a front edge of the inferior quadrant of the crystalline lens believed to contain AGEs, the point on the crystalline lens being identified based on the step of computing the location of the center of the subject's pupil, the illumination being made with excitation radiation to conduct a scan of the optical reflectance thereof, the illuminating comprising:
   generating the excitation radiation using a blue light emitting diode;
   passing the excitation radiation through an aperture;
   after passing the excitation radiation through the aperture, passing the excitation radiation through a blue bandpass filter;
   after passing the excitation radiation through the blue bandpass filter, passing the excitation radiation through focusing lenses without passing the excitation radiation through a beam splitter or dichroitic mirror; and directing the focused excitation radiation to the point on the crystalline lens of the subject's eye;
   (3) tracking the location of the center of the pupil during the scan;
   (4) detecting a fluorescent radiation emission intensity that is backscattered from the lens or a fluorescent lifetime of fluorescent radiation generated by the lens in response to the excitation radiation at one or more excitation wavelengths, wherein the fluorescent light is generated by the AGEs in the illuminated lens of the eye, the detecting comprising:
   receiving the fluorescent radiation backscattered or generated from the lens by a collection lens; directing the fluorescent radiation backscattered or generated from the lens through a red and IR blocking filter after received by the collection lens; and directing the filtered radiation to a photodetector;
   (5) normalizing the fluorescent radiation emission intensity that is backscattered from the lens or a fluorescent lifetime of fluorescent radiation of (4) to determine a peak intensity of the fluorescent component of the detected fluorescent radiation emission;
   (6) providing the normalized data to a computer subsystem encoded with an algorithm including pre-determined look up tables of (a) an expected fluorescent radiation emission intensity that is backscattered from the lens or the fluorescent lifetime of fluorescent radiation from the lenses of individuals without the medical condition and (b) one or more expected health characteristics selected from the group consisting of body mass index (BMI), waist circumference, HbAlc levels, suitable biomarker level or history of smoking, high blood pressure, high cholesterol, dry eye or family experience of the medical condition among individuals without the medical condition and of a corresponding age, gender, height, weight and ethnicity of the subject;
   (7) comparing (a) the fluorescent emission intensity that is backscattered from the lens or the fluorescent lifetime of the detected fluorescent radiation to the expected fluorescent radiation emission of (6), and (b) one or more of body mass index (BMI), waist circumference, HbAlc, suitable biomarker level or history of smoking, high blood pressure, high cholesterol, dry eye and family experience of the medical condition of the subject to the one or more expected health characteristics; and
   (8) determining the disease state experienced by the subject based on results of the comparing step;
   wherein the illuminating step comprises automatically directing focused excitation radiation to the lens at an area that is offset from the center of the pupil based on the tracked location of the center of the pupil.

2. The method of claim 1, wherein the detecting step comprises detecting the fluorescent radiation generated by the crystalline lens using at least one of an intensity based technique, a phase-shift technique, and a polar anisotropy technique.

3. The method according to claim 1, wherein the normalization of step (6) comprises normalization of the fluorescent light by dividing fluorescent signal by the total returned signal consisting of the fluorescent signal plus the scattered signal.

4. The method according to claim 1, further comprising the step of reporting a level of confidence in the accuracy of the determination of the disease state.

5. The method according to claim 1, wherein step (2) comprises illuminating a point on a crystalline lens of the subject's eye 65 to 75% inferior from a front edge of the crystalline lens with excitation radiation to conduct a scan of the optical reflectance thereof.

6. The method according to claim 1 further comprising a second illumination step and a second detecting step; comparing the detected radiation of the second detecting step to the detecting step, and confirming the two detecting steps provide results within a predetermined consistency percentage.

7. The method of claim 6 wherein the predetermined consistency percentage is 20%, and further comprising the steps of determining a lens thickness and a pupil diameter, and rejecting data from the detecting step and second detecting step if the determined thickness and diameter are outside of a normal range.

* * * * *